United States Patent [19]

Fukuchi et al.

[11] Patent Number: 4,831,250
[45] Date of Patent: May 16, 1989

[54] APPARATUS FOR DETECTING DEFECTS ON BOTTLE MOUTH WITH SCREW THREAD

[75] Inventors: Hiroyuke Fukuchi; Masatoshi Nishiyama; Yukio Sugawara, all of Tokyo, Japan

[73] Assignee: Kirin Beer Kabushiki Kaisha, Tokyo, Japan

[21] Appl. No.: 106,583

[22] Filed: Oct. 8, 1987

[30] Foreign Application Priority Data

Oct. 13, 1986 [JP] Japan ................................. 61-242693

[51] Int. Cl.⁴ .............................................. G01H 9/04
[52] U.S. Cl. ................................ 250/223 B; 356/428; 356/240
[58] Field of Search .................... 250/223 B; 209/526, 209/524; 356/240, 428

[56] References Cited

U.S. PATENT DOCUMENTS 4,213,702 7/1980 Bryant et al. .................... 250/223 B
4,492,476 1/1985 Miyazawa ........................ 250/223 B
4,601,395 7/1986 Juvinall et al. ................... 250/223 B
4,606,635 8/1986 Miyazawa et al. ............... 250/223 B
4,650,326 3/1987 Nagamine et al. ................. 209/526
4,679,075 7/1987 Williams et al. ................ 250/223 B
4,701,612 10/1987 Sturgill ................................. 209/526

Primary Examiner—Edward P. Westin
Assistant Examiner—Khaled Shami
Attorney, Agent, or Firm—Ladas & Parry

[57] ABSTRACT

An apparatus for detecting defects on a bottle mouth having a screw thread has an illuminating unit for applying light to the mouth of a bottle under rotation; a photoelectric conversion unit for photoelectrically converting a light transmitted image of the bottle mouth illuminated with light by the illuminating unit into electric signals; a defect detecing unit for detecting a defect within a predetermined area in the light transmitted image photoelectrically converted by the photoelectric conversion unit, based on the brightness at predetermined at-least two points in a predetermined detection direction within the area; and a judge unit for calculating the number of defects detected by the defect detecting unit and judging the presence of any defect of the bottle mouth based on the number of defects.

The apparatus detects defect points from the light transmitted image of the bottle mouth and judges based on the number of defect points whether or not there is a defect of a bottle.

12 Claims, 6 Drawing Sheets

APPARATUS FOR DETECTING DEFECTS ON BOTTLE MOUTH WITH SCREW THREAD

BACKGROUND OF THE INVENTION

The present invention relates to an apparatus for detecting defects on a bottle mouth having a screw thread, such as stones, voids, breakages, cracks, foreign materials stuck to the bottle mouth, stains or deformed threads.

Glass bottles used for filling with liquor, refreshing drink, food or the like must be inspected as to whether there is any defect irrespective of whether they are new ones just manufactured by a bottle maker or old ones being recirculated. Portions of a bottle to be inspected include its body, bottom, mouth with a screw thread. If there is any defect at the bottle mouth, sealing of the bottle becomes insufficient and hence resulting in a possible problem of food sanitation. Therefore, bottles with such defect must be rejected.

It is difficult, however, to inspect bottle mouths because of their complicated shape and various thread patterns. It is also difficult to distinguish a normal thread configuration from a defect. Because of the above difficulties, in spite of a necessity of inspecting bottle mouths, a bottle mouth inspecting apparatus available in practice has not been provided.

SUMMARY OF THE INVENTION

It is an object of the present invention to provide an apparatus capable of correctly detecting any defect on a bottle mouth having a screw thread at high speed.

To achieve the above object, the present invention provides an apparatus for detecting defects on a bottle mouth having a screw thread, comprising: illuminating means for: illuminating the mouth of a bottle under rotation; photoelectric conversion means for photoelectrically converting a light transmitted image of said bottle mouth illuminated with uniformly diffused light; by said illuminating means into electric signals; defect detecting means for detecting a defect within a predetermined area in said light transmitted image photoelectrically converted by said photoelectric conversion means, based on the brightness at predetermined at-least two points in a predetermined detection direction within said area said direction being inclined with a certain inclination representing a direction of the thread; and judge means for calculating the number of defects detected by said defect detecting means and judging the presence of any defect of said bottle mouth based on the number of defects.

DETAILED DESCRIPTION OF THE INVENTION

Figure 1:
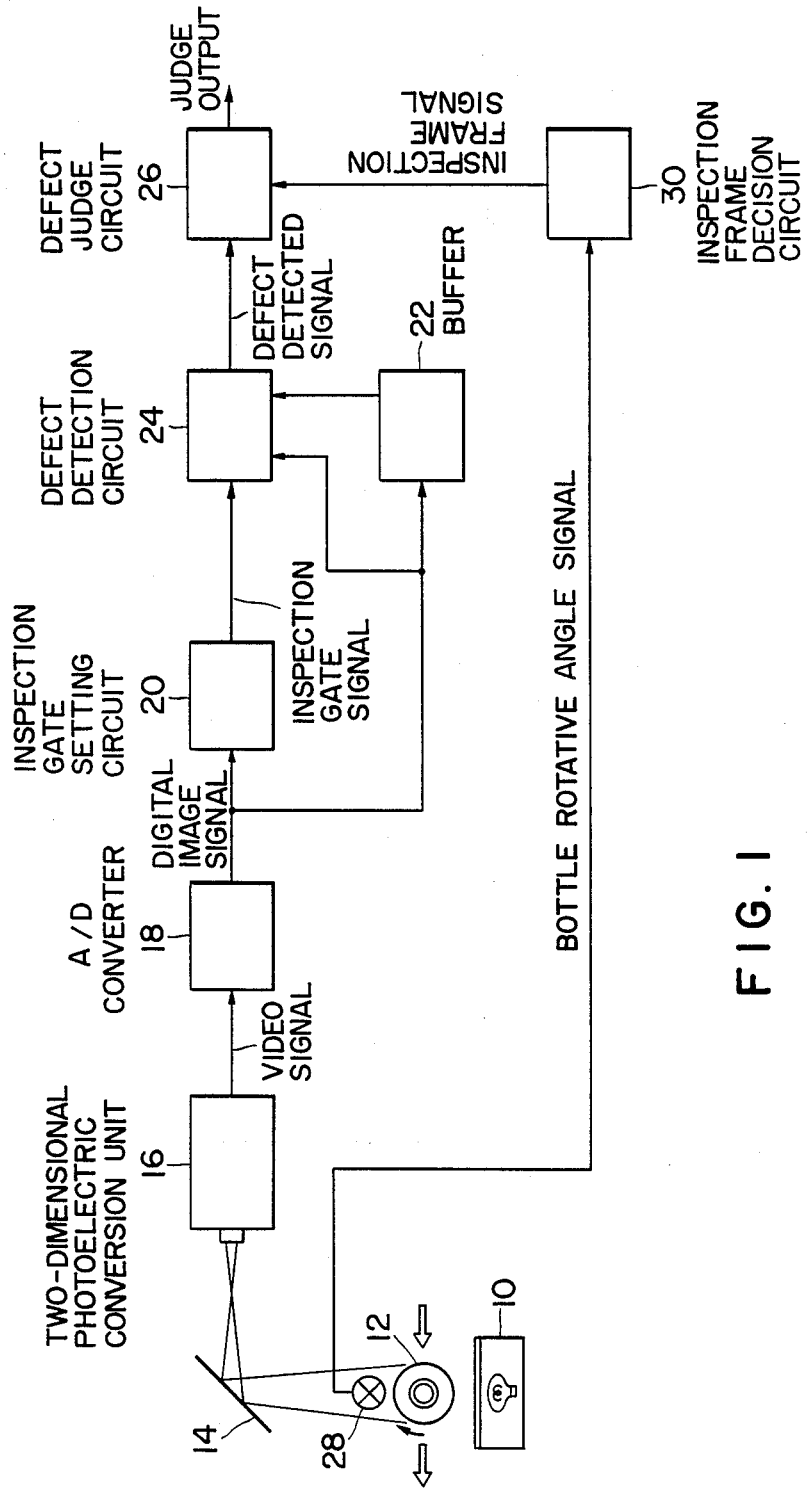
FIG. 1 is a block diagram showing an embodiment of the apparatus for detecting defects on a bottle mouth having a screw thread according to the present invention.
Figure 2:
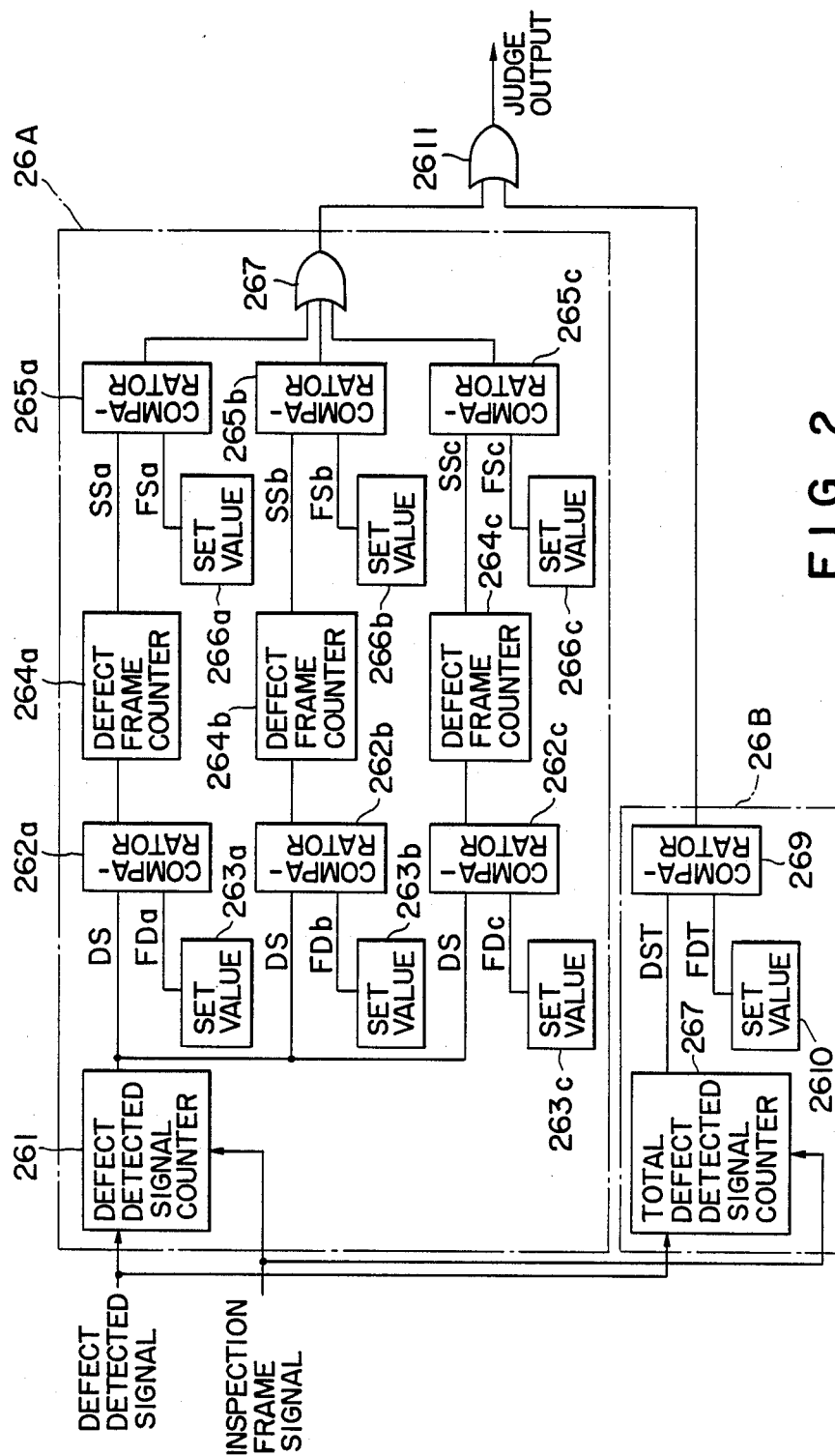
FIG. 2 is a detailed block diagram showing the defect judge circuit of the apparatus according to the present invention.
Figure 3:
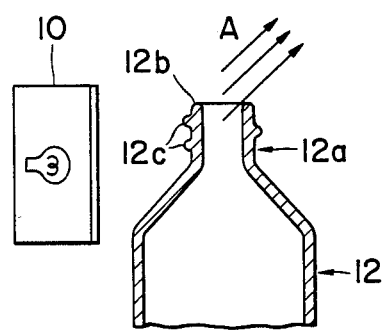
FIG. 3 illustrates the direction of light rays of an image which are inputted to the two-dimensional photoelectric conversion unit of the apparatus according to the present invention.

FIGS. 1 and 2 show an embodiment of the apparatus for detecting defects on a bottle mouth having a screw thread according to the present invention. In this embodiment, a bottle 12 to be inspected is conveyed while being rotated. The bottle 12 is illuminated with uniformly diffused light by means of a diffused light source 10 having a radiation surface capable of radiating uniformly diffusion light. A light transmitted image of the mouth of the bottle 12 having a screw thread is incident to a two-dimensional photoelectric conversion unit 16 via a viabratory mirror 14. The vibratory mirror 14 is caused to move in synchronism with the motion of the bottle 12.

Specifically, the vibratory mirror 14 tracks the running bottle 12 such that the light transmitted image of the mouth of the bottle 12 becomes incident just to The two-dimensional photoelectric conversion unit 16 may be a CCD camera for converting the light transmitted image of the mouth 12a of the bottle 12 into analog electric signals.

The two-dimensional photoelectric conversion unit 16 is mounted at the position where light from the mouth 12a of the bottle 12 in the direction indicated by an arrow becomes incident to the unit 16. Thus, an image of the mouth 12a of the bottle 12 as viewed at an inclination from the upper position, as shown in FIG. 4, is applied to the two-dimensional photoelectric conversion unit 16.

The two-dimensional photoelectric conversion unit 16 may be mounted at the position where it can view the mouth 12a of the bottle 12 at an inclination from the lower position, to obtain a light transmitted image on the front side of the bottle mouth 12a.

Figure 4:
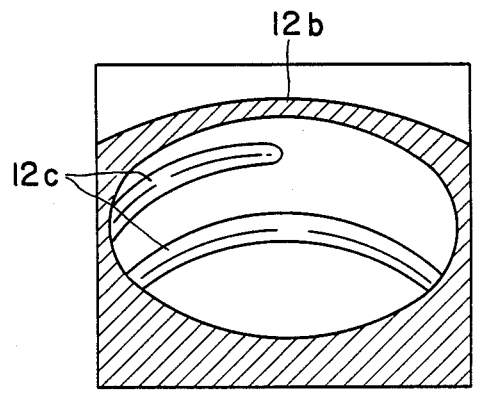
FIG. 4 shows an example of a light transmitted image of a bottle obtained in the apparatus according to the present invention.
Figure 5:
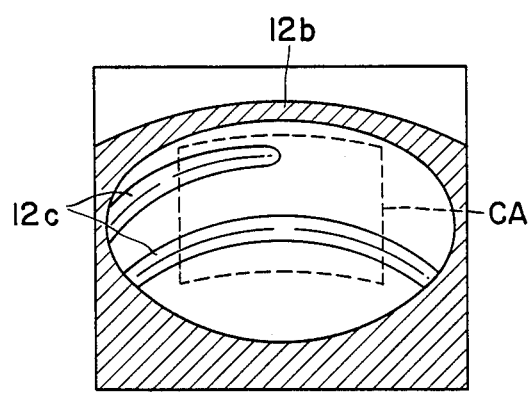
FIG. 5 shows an example of an inspection area of a light transmitted image of a bottle used by the apparatus according to the present invention.

The two-dimensional photoelectric conversion unit 16 is scanned, for example, from the upper portion to the lower portion and from the left to the right of a light transmitted image shown in FIG. 4. In the light transmitted image, a hatched portion represents the top 12b of the mouth 12a of the bottle 12, the mouth 12a becomes white as a whole, and the boundaries of the thread 12c appear as a black line.

An A/D converter 18 converts the analog video signal from the two-dimensional conversion unit 16 into a digital video signal having a predetermined number of bits. The digital video signal is outputted to an inspection gate setting circuit 20, a buffer 22 and a defect detection circuit 24.

The inspection gate setting circuit 20 is used for determining an area within a light transmitted image as shown in FIG. 4 for the detection of a defect by the defect detection circuit 24 to be described later. In this embodiment, an inspection area CA at the middle of bottle mouth 12a and below the top 12b of the bottle mouth 12a is used for detection. The inspection gate setting circuit 20 detects the top 12b of the bottle mouth 12a based on inputted digital video signals to thereby output a gate signal which allows those digital video signals remote from the detection point of the top 12b and having a predetermined length to pass therethrough. The detection of the top 12b of the bottle mouth 12a can be performed, for example, by detecting a first black signal obtained during scanning from the upper portion of the light transmitted image. The right and left edges of the inspection area CA are defined by the predetermined positions in the entire light transmitted image.

The right and left edges of the inspection area CA may also be defined by detecting the positions of the right and left edges of the bottle mouth with the screw thread from a light transmitted image covering the entirety of the mouth 12a of the bottle 12.

The digital video signals from within the inspection area CA which are required for the defect detection by the defect detection circuit 24 are stored in the buffer 22.

Figure 6A:
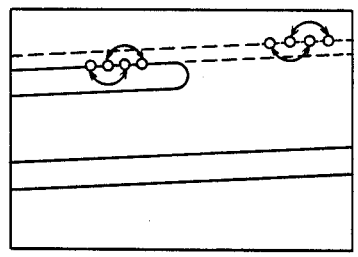
FIGS. 6(A) and 6(B), 7(A) and 7(B), and 8(A), 8(B) and 8(C) are views used for explaining the defect detection method employed in the apparatus according to the present invention.
Figure 7A:
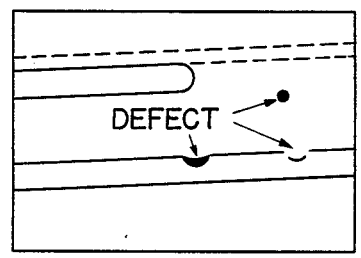

The defect detection circuit 24 re-arranges the digital video signals within the inspection area CA using as an apparent reference the upper edge of a rectangular shape of the inspection area CA as shown in FIGS. 6(A) and 7(A). As a result, images of the threads 12c are represented as parallel lines with a certain inclination within the inspection area CA. The defect detection circuit 24 compares and calculates the brightness of at least two points spaced by a constant distance along the parallel lines 6, thereby detecting a defect. The methods of comparison and calculation may include various types:

(1) A defect is assumed to be present if the following formula stands wherein the brightness of two points subjected to the comparison and calculation are Q1 and Q2.

$$|Q1-Q2| \geq (\text{constant A})$$

(2) A defect is assumed to be present if the following formula stands wherein the brightness of three points spaced apart by a constant distance along the parallel lines are Q1, Q2 and Q3.

$$|Q2-[Q1+Q3]/2| \geq (\text{constant B})$$

(3) A defect is assumed to be present if any one of the following formulas stands wherein the brightness of two points subjected to the comparison and calculation are Q1 and Q2.

$$Q1/Q2 \geq (\text{constant C})$$

$$Q1/Q2 \leq 1/(\text{constant C})$$

(4) A defect is assumed to be present if any one of the following formulas stands wherein the brightness of three points spaced apart by a constant distance along the parallel lines are Q1, Q2 and Q3.

$$Q2/[(Q1+Q3)/2] \geq (\text{constant D})$$

$$Q2/[(Q1+Q3)/2] \leq 1/(\text{constant D})$$

The inclination of parallel lines along which a defect is to be detected, the distance between points subjected to the comparison and calculation, the constants A, B, C and D in the above formulas, are all determined beforehand based on the types of bottles. The constants C and D are decided as a number greater than 1, for example, 2.

Figure 6B:
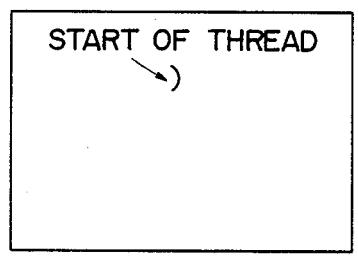
Figure 7B:
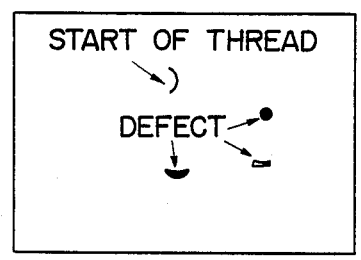

FIGS. 6(A), 6(B) and 7(A), 7(B) illustrate how a defect is detected through the comparison and calculation of two or three points along the parallel lines. For the light transmitted images of FIGS. 6(A) and 7(A), defect detected points as shown in FIGS. 6(B) and 7(B) are obtained. Even if an actual defect is not present, a defect detected point appears at the start or end of the thread 12c as shown in FIGS. 6(B) and 7(B). Therefore, actual defect points are those excepting the points corresponding to the start and end of the thread 12c, as specifically shown in FIG. 7(B).

The defect judge circuit 26 judges a defect for each inspection frame which is sampled upon an inspection frame decision signal from an inspection frame decision circuit 30. The inspection frame decision circuit 30 outputs an inspection frame decision signal at each predetermined rotative angle of the bottle 12, based upon a bottle rotative angle signal from a bottle rotative angle detector 28. For instance, if an inspection frame signal is outputted to the defect judge circuit 26 at each increase in bottle rotative angle by 3.6 degree, a defect is inspected for in 100 frames per one rotation of the bottle 12.

Referring to FIG. 2, the defect judge circuit 26 includes a first defect judge circuit 26A and a second defect judge circuit 26B, whereby an inspection frame which is sampled upon an inspection frame signal from the inspection frame decision circuit, 30 is inspected as to whether there is an actual defect of an inspected bottle, based on defect detected signals from the defect detection circuit 24.

First the description will be directed to the first defect judge circuit 26A. A defect detected signal counter 261 counts the number of defect detected signals for an inspection frame corresponding to an inspection frame signal inputted thereto. By counting the number of defect detected signals for an inspection frame, the sum DS of defect detected points of that inspection frame is obtained. The sum DS is compared with set values FDa, FDb and FDc respectively set at value setters 263a, 263b and 263c by means of comparators 262a, 262b and 262c. If the sum DS is decided larger than the set values FDa, FDb and FDc by the comparators 262a, 262b and 262c, a defect frame signal is outputted which represents that the inspection frame is defective. Each defect frame signal is outputted to each of defect frame counters 264a, 264b and 264c to count the number of defect frame signals. Namely, the defect frame counter 264a, 264b and 264c each count the number of defective frames as judged by each of the comparators 262a, 262b and 262c. The counts SSa, SSb and SSc of the defect frame counters 264a, 264b and 264c are compared with set values FSa, FSb and FSc respectively set at constant setters 266a, 266b and 266c by means of comparators 265a, 265b and 265c. If the comparators 265a, 265b and 265c each decide that each of the counts SSa, SSb and SSc is greater than corresponding one of the set values FSa, FSb and FSc, a defect signal is outputted therefrom which represents that the bottle 12 is defective. As a result, if any one of the comparators 265a, 265b and 265c outputs a defect signal, an OR gate 267 passes the defect signal.

The set values FDa, FDb and FDc for the number of defect detected points and the set values FSa, FSb and FSc for the number of defective frames are determined beforehand based on the types of bottles 12. By properly setting these set values FDa, FDb and FDc, and FSa, FSb and FSc, it is possible to correctly judge whether the bottle is defective even if the start and end of the thread 12c are included in the number of defect detected points. For example, assuming that the number of defect detected points of the start and end of the thread 12c is smaller than 5, and that the start or end of the thread 12c is detected from 10 frames among 100 inspection frames, the set values are determined as FDa=6, FSa=11; FDb=4, FSb=15, and FDc=10, FSc=2. Particularly, if there are more than 11 defective frames each having more than 6 defect detected points, then it is judged that there is an actual defect or defects excepting those corresponding to the start or end of the thread 12c. Further if there are defective frames as large as 15 each having more than 4 defect detected points, then it is judged that there is an actual defect or defects irrespective of a small number of defect detected points. Furthermore, if there are more than 10 defect detected points, it is judged in spite of about 2 defective frames that there is an actual defect or defects since it cannot be considered that such a large number of defect detected points should include only those corresponding to the start and end of the thread 12c.

Next, the description for the second defect judge circuit 26B will be given. A total defect detected signal counter 268 counts defect detected signals for all the inspection frames corresponding to inspection frame signals. The count DST of the total defect detected signal counter 268 is compared with a set value FDT set by a constant setter 2610 by means of a comparator 269. If the comparator 269 decides that the count DST is greater than the set value FDT, a defect signal is outputted therefrom.

The set value FDT is determined beforehand based on the types of bottles. In this embodiment, the set value is determined as FDT=50. Namely, if all the defect detected points reach more than 50, then it is judged that such a number includes not only the defect detected points corresponding to the start or end of the thread 12c itself but also an actual defect or defects.

The outputs from the first and second defect judge circuits 26A and 26B are supplied to an OR gate 2611 which in turn outputs a final judge signal.

As seen from the above embodiment, an actual defect or defects on a bottle mouth with a screw thread can be found correctly even if defect detected points for the start or end of the thread 12c are included.

Figure 8A:
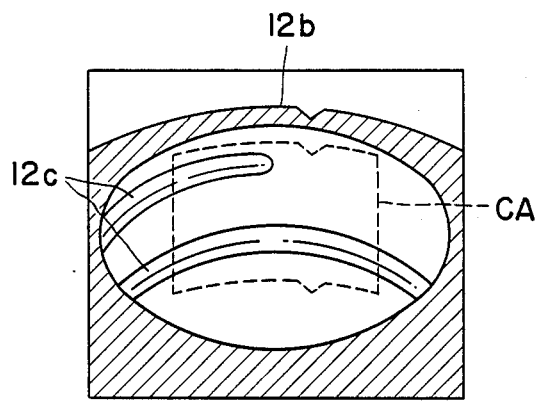
Figure 8B:
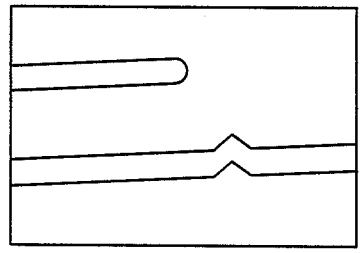
Figure 8C:
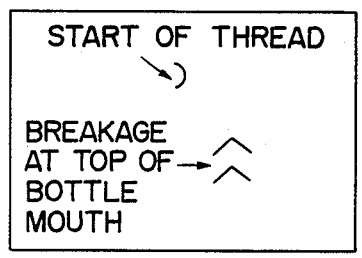

The above embodiment may be used for the detection of defects such as breakages on the top 12b of the bottle mouth at the threaded bottleneck 12a. Particularly, if a breakage is present on the top 12b of a bottle mouth as shown in FIG. 8(A), the top and bottom edges of the inspection area CA are bent due to the presence of the breakage. After re-arranging of the video signals within the inspection area CA by the defect detection circuit 24 using the top edge of the area as a reference, obtained is a thread 12c image with a portion thereof bent as shown in FIG. 8(B). With a defect detection of this inspection frame, there appear defect detected points as shown in FIG. 8(C), based on which points it is possible to judge a defect or defects of the top of the bottle mouth.

Figure 9:
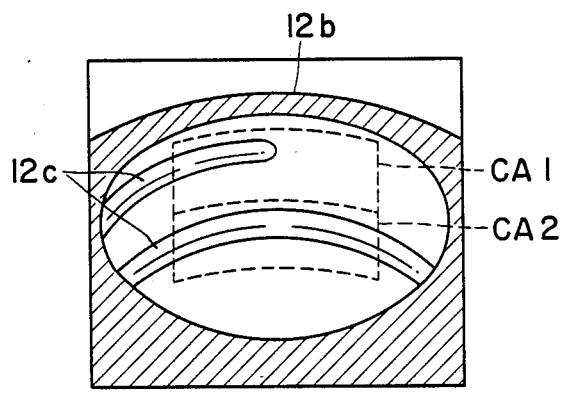
FIGS. 9 and 10 show other examples of inspection areas of light transmitted images of bottles used by the apparatus according to the present invention.
Figure 10:
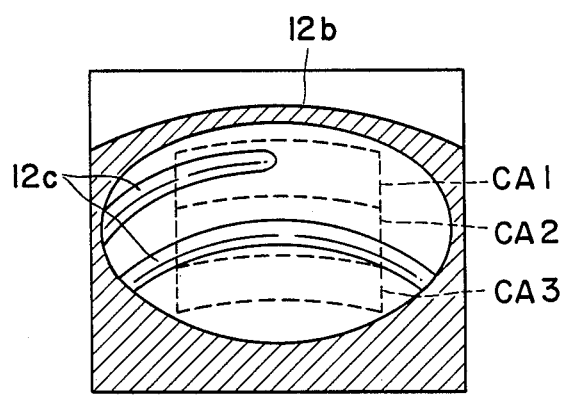

Although a single inspection area CA has been used in the above embodiment for the defect inspection, the inspection area may be divided into a plurality of areas. For example, as shown in FIG. 9, the inspection area CA may be divided into upper and lower inspection areas CA1 and CA2. The two inspection areas CA1 and CA2 each are provided with a defect judge circuit 26. The start of the thread is occupied by the upper inspection area CA1, while the end and intermediate of the thread are occupied by the lower inspection area CA2. Assuming that the number of defect detected points for the start of the thread is larger than that for the end of the thread, the defect detection sensitivity for the lower inspection area CA2 may be set high. Alternatively as shown in FIG. 10, the inspection area CA may be divided into upper, middle and lower inspection areas CA1, CA2 and CA3. Assuming that the number of defect detected points for the end of the thread is smaller than that for the start of the thread, the defect detection sensitivity for the inspection area CA2 occupying the intermediate portion of the thread may be set higher than the sensitivity for the inspection areas CA1 and CA2 respectively occupying the start and end of the thread.

It is preferable to make the boundaries of the inspection areas CA1, CA2 and CA3 overlap upon each other for the purpose of precise defect detection at the boundaries.

The first and second defect judge circuits 26A and 26B have been used as the defect judge circuit 26 for the defect judgement of a bottle in the above embodiment. However, only one of both the defect judge circuits may be used for obtaining such judgement. Further, although the number of defective frames having a larger number of defect detected points have been counted in the above embodiment, the number of defective frames having a smaller number of defect detected points may be counted for the judgement of bottle defect. The combination of both judgement schemes may be applied.

Furthermore, the inspection gate setting circuit 20 has been used for determining the inspection area of a light transmitted image in the above embodiment. However, the inspection area may be fixed on condition that the position of a bottle does not vary to a large extent.

Still further, if the transfer speed and rotational speed of a bottle to be inspected is constant, the bottle rotative angle detector 28 and the inspection frame decision circuit 30 are not needed. In such a case, the inspection frame may be defined in synchronism with the vibratory mirror 14 or at the interval of constant time periods.

Figure 11:
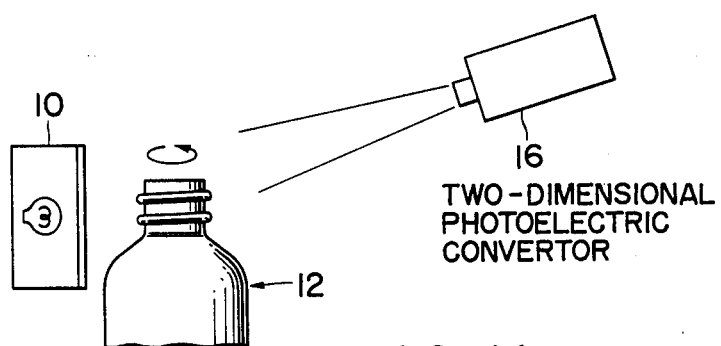
FIG. 11 illustrates another embodiment of the apparatus for detecting defects on a bottle mouth having a screw thread according to the present invention.

If a bottle 12 is rotated at a fixed position as shown in FIG. 11, the rotational speed of the bottle 12 maintains precisely at a certain speed so that there is no problem of using the inspection frame definition at the interval of constant time periods.

Obviously, the present invention is not intended to be limited to the above embodiment only, but various modifications are possible.

As apparent from the foregoing description of the present invention, it becomes possible to correctly inspect a defect on a bottle mouth having a screw thread at a high speed.

What is claimed is:

1. An apparatus for detecting defects on a bottle mouth with a screw thread, comprising:

illuminating means for illuminating the mouth of a bottle under rotation;

photoelectric conversion means for photoelectrically converting a light transmitted image of said bottle mouth illuminated with uniformly diffused light by said illuminating means into electric signals;

defect detecting means for detecting a defect, within a predetermined area in said light transmitted image photoelectrically converted by said photoelectric conversion means, based on the brightness at predetermined at-least two points in a predetermined detection direction within said area, said direction being inclined with a certain inclination representing a direction of the thread; and judge means for calculating the number of defects detected by said defect detecting means and judging the presence of any defect of said bottle mouth based on the number of defects.

2. An apparatus according to claim 1, further comprising detection area decision means for declining said predetermined area, which is defined at the middle of and below the top of the bottle mouth, to be detected by said defect detection means, based on said light transmitted image of said bottle mouth.

3. An apparatus according to claim 1, further comprising rotative angle detector means for detecting a rotative angle of said bottle, and inspection frame decision means responsive to said rotative angle detected by said rotative angle detector means for deciding a plurality of inspection frames based on which said judge means judges a defect.

4. An apparatus accordingly to claim 2, further comprising rotative angle detector means for detecting a rotative angle of said bottle, and inspection frame decision means responsive to said rotative angle detected by said rotative angle detector means for deciding a plurality of inspection frames based on which said judge means judges a defect.

5. An apparatus according to claim 1, wherein said judge means judges a defect based on whether there are more than a predetermined number of inspection frames in a measurement each of said inspection frames having more than a predetermined number of defect points.

6. An apparatus according to claim 2, wherein said judge means judges a defect based on whether there are more than a predetermined number of inspection frames in a measurement each of said inspection frames having more than a predetermined number of defect points.

7. An apparatus according to claim 3, wherein said judge means judges a defect based on whether there are more than a predetermined number of inspection frames in a measurement each of said inspection frames having more than a predetermined number of defect points.

8. An apparatus according to claim 4, wherein said judge means judges a defect based on whether there are more than a predetermined number of inspection frames in a measurement each of said inspection frames having more than a predetermined number of defect points.

9. An apparatus according to claim 1, wherein said judge means judges a defect based on whether there are more than a predetermined number of defects in all the inspection frames in a measurement.

10. An apparatus according to claim 2, wherein said judge means judges a defect based on whether there are more than a predetermined number of defects in all the inspection frames in a measurement.

11. An apparatus according to claim 3, wherein said judge means judges a defect based on whether there are more than a predetermined number of defects in all the inspection frames.

12. An apparatus according to claim 4, wherein said judge means judges a defect based on whether there are more than a predetermined number of defects in all the inspection frames.

* * * * *